United States Patent
Lin et al.

(10) Patent No.: US 11,020,445 B2
(45) Date of Patent: Jun. 1, 2021

(54) METHOD FOR REDUCING THE CONTENT OF HEAVY METALS IN BLOOD AND IMPROVING THE PULMONARY FUNCTION USING GREEN PEAR FRUITLET EXTRACT

(71) Applicant: TCI CO., LTD., Taipei (TW)

(72) Inventors: Yung-Hsiang Lin, Taipei (TW);
Yu-Ting Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 462 days.

(21) Appl. No.: 16/174,573

(22) Filed: Oct. 30, 2018

(65) Prior Publication Data

US 2019/0134134 A1 May 9, 2019

Related U.S. Application Data

(60) Provisional application No. 62/583,124, filed on Nov. 8, 2017.

(51) Int. Cl.
*A61K 36/73* (2006.01)
*A61P 39/00* (2006.01)
*A61P 11/00* (2006.01)

(52) U.S. Cl.
CPC .............. *A61K 36/73* (2013.01); *A61P 11/00* (2018.01); *A61P 39/00* (2018.01); *A61K 2236/00* (2013.01)

(58) Field of Classification Search
CPC ..... A61K 2236/00; A61K 36/73; A61P 11/00; A61P 39/00
See application file for complete search history.

(56) References Cited

FOREIGN PATENT DOCUMENTS

| CN | 106389784 A | 2/2017 |
|----|-------------|--------|
| CN | 107307236 A | 11/2017 |
| TW | M549622 U | 10/2017 |

OTHER PUBLICATIONS

Sun L, et al "Characterization and Quantification of Polyphenols and Triterpenoids in Thinned Young Fruits of Ten Pear Varieties by UPLC-QTRAP-MS/MS" Molecules, Jan. 3, 2019, 24(1), 159, 21 pages; doi: 10.3390/molecules24010159. (Year: 2019).*

Protective and prophylactic effects of chlorogenic acid aluminum-induced acute hepatotoxicity and hematotoxicity in mice. Cheng Dai et al., pp. 125-132, especially in the right coumn of p. 125 to the left column of p. 126, Results paragraph and p. 131, Chemico-Biological Interactions 273 (2017).

The protective effect of chlorogenic acid on arsenic troxide induced hepatotoxicity in mice. Javad Ghahhari et al., pp. 165-172, especially Results and Discussion paragraph (p. 167). Bioscience Biotechnology Research Communications 10 (2017).

Advances in studies on chemical constituents in medicinal plants of *Pyrus L.* and their pharmacological activities. Zhang Jing et al., pp. 2077-2082. vol. 43, No. 10, Chinese Traditional and Herbal Drugs (Oct. 2012).

Neuroprotective effects of chlorogenic acid against apoptosis of PC12 cells induced by methymercury. Yongjin Li et al., pp. 13-21, Environmental Toxicology and Pharmacology 26 (2008).

Examination report dated Aug. 25, 2020, listed in correspondent Taiwan patent application No. 107137398 (publication No. TW201918256).

* cited by examiner

*Primary Examiner* — Aaron J Kosar

(74) *Attorney, Agent, or Firm* — Chieh-Mei Wang

(57) ABSTRACT

The present invention provides a method for reducing the content of heavy metals in blood and improving the pulmonary function using green pear fruitlet extract. The green pear fruitlet extract can effectively reduce the content of harmful heavy metals in human body to prevent the harmful effects of heavy metals, and improve forced vital capacity and the peak expiratory flow of humans to reduce the respiratory resistance and increase the expiratory flow. The green pear fruitlet extract is prepared by extracting green pear fruitlet using water, alcohol, or a mixture of water and alcohol as a solvent.

15 Claims, 3 Drawing Sheets

METHOD FOR REDUCING THE CONTENT OF HEAVY METALS IN BLOOD AND IMPROVING THE PULMONARY FUNCTION USING GREEN PEAR FRUITLET EXTRACT

CROSS-REFERENCE TO RELATED APPLICATION

This application claims priority of U.S. provisional application No. 62/583,124, filed on Nov. 8, 2017 the content of which is incorporated herein in its entirety by reference

BACKGROUND OF THE INVENTION

1. Field of the Invention

The present invention relates to a method of using green pear fruitlet extract, and more particularly to a method for reducing the content of heavy metals in the blood and improving the pulmonary function by using a green pear fruitlet extract.

2. The Prior Art

Heavy metals refer to a group of metal elements with a density exceeding 5 grams per cubic centimeter. Metals or metalloid elements that are obviously toxic to living things are heavy metals, including: hydrargyrum, gold, chromium, copper, cadmium, zinc, lead, etc. Although arsenic is non-metallic, arsenic is obviously toxic to organisms, so arsenic is also listed in heavy metals. The environment is filled with heavy metals such as smoking, second-hand smoke, insecticides, hair dyes, cosmetics, fillings, toys, Chinese medicine, medicines, chemical fertilizers, seafood, and waste gas.

Heavy metals enter the human body through diet, breathing or direct contact. However, heavy metals are not as catabolized and excreted in the liver as other toxins. They are cumulative in the kidneys, pancreas, bones, nervous system, hematopoietic system, endocrine system, skin and mucous membranes continue to accumulate. After accumulating a certain amount, it will directly damage organ tissues and produce symptoms of various clinical diseases such as nausea, diarrhea and burnout. Heavy metal poisoning can be treated by chelation therapy or by blood-washing therapy to eliminate harmful heavy metals. However, in the process of chelation therapy or blood-washing therapy, essential minerals such as calcium, magnesium, zinc, etc. may also be lost.

The lung is an important organ of the respiratory system and it is mainly responsible for the gas exchange work in human bodies. When inhaling, the diaphragm is pressed down and the ribs are moved upwards to inhale gas into lungs; when exhaling, the diaphragm is rebounded and the ribs are moved downwards to exhaust gas from lungs. When the breathing is normal, the blood of the whole body will be smooth. If the normal function of the lung is dysfunctional, the function of sucking will be weakened. If it lasts for a long time, the body will be in a state of chronic hypoxia, forming a deficiency and becoming tired. The effects not only end in the respiratory system, but also affect the body's water metabolism, blood circulation, immune system and other functions.

In the top 10 causes of death in Taiwan, lung-related illnesses accounted for two (pneumonia and lower respiratory tract infections). By 2013, pneumonia was the fourth highest cause of death. Therefore, the health of the lungs is even more important. However, most of the current health care for the lungs can only start from improving living habits, exercising more or staying away from smoke and exhaust pollution, and there is no effective and direct method to improve lung health.

In view of the above, in order to prevent the harm of heavy metals to human bodies and improve the health of lungs, and based on the improvement of modern living standards and the improvement of the concept of health care, it is necessary to develop a novel composition that can reduce the content of heavy metals in the blood and improve the pulmonary function.

SUMMARY OF THE INVENTION

To solve the foregoing problem, one objective of the present invention is to provide a method for reducing the content of a heavy metal in the blood, comprising administering to a subject in need thereof a composition comprising a green pear fruitlet extract, wherein the green pear fruitlet extract is prepared by extracting a green pear fruitlet using water, alcohol, or a mixture of water and alcohol as a solvent, preferably water.

The other objective of the present invention is to provide a method for improving the pulmonary function, comprising administering to a subject in need thereof a composition comprising a green pear fruitlet extract, wherein the green pear fruitlet extract is prepared by extracting green pear fruitlet using water, alcohol, or a mixture of water and alcohol as a solvent, preferably water.

In one embodiment of the present invention, the heavy metal is hydrargyrum or arsenic, and the green pear fruitlet extract is administered at a daily dosage of at least 5-10 g.

In one embodiment of the present invention, the green pear fruitlet extract reduces the respiratory resistance and/or increases the expiratory flow of the subject in need thereof, and the green pear fruitlet extract increases the forced vital capacity (FVC) and the peak expiratory flow (PEF) of the subject in need thereof, and the green pear fruitlet extract is administered at a daily dosage of at least 5-10 g.

In one embodiment of the present invention, a liquid-to-solid ratio of the solvent to the green pear fruitlet is from 10:1 to 1:1, and the green pear fruitlet is extracted at a temperature from 70-95° C.

The green pear fruitlet extract of the present invention not only can effectively reduce the content of harmful heavy metals in human body such as hydrargyrum and arsenic, which are common in air pollution, but also can effectively improve forced vital capacity and the peak expiratory flow of humans to reduce the respiratory resistance and increase the expiratory flow. The green pear fruitlet extract of the present invention has the effects of preventing the harmful effects of heavy metals, smoothing the breathing and improving the pulmonary function. Therefore, the green pear fruitlet extract of the present invention can be used for preparing a composition for reducing the content of heavy metals in the blood and for improving the pulmonary function. When the green pear fruitlet extract of the present invention is prepared as a composition, the composition is in a form selected from the group consisting of powder, granules, liquid, colloid, and cream. The composition can be made into, but is not limited to, a food, a drink, a drug, a reagent or a nutritional supplement, which is administered to the body by oral administration, skin application, etc.

The following drawings form part of the present specification and are included here to further demonstrate some aspects of the present invention, which can be better under-

DETAILED DESCRIPTION OF THE PREFERRED EMBODIMENT

Definition

Figure 1:
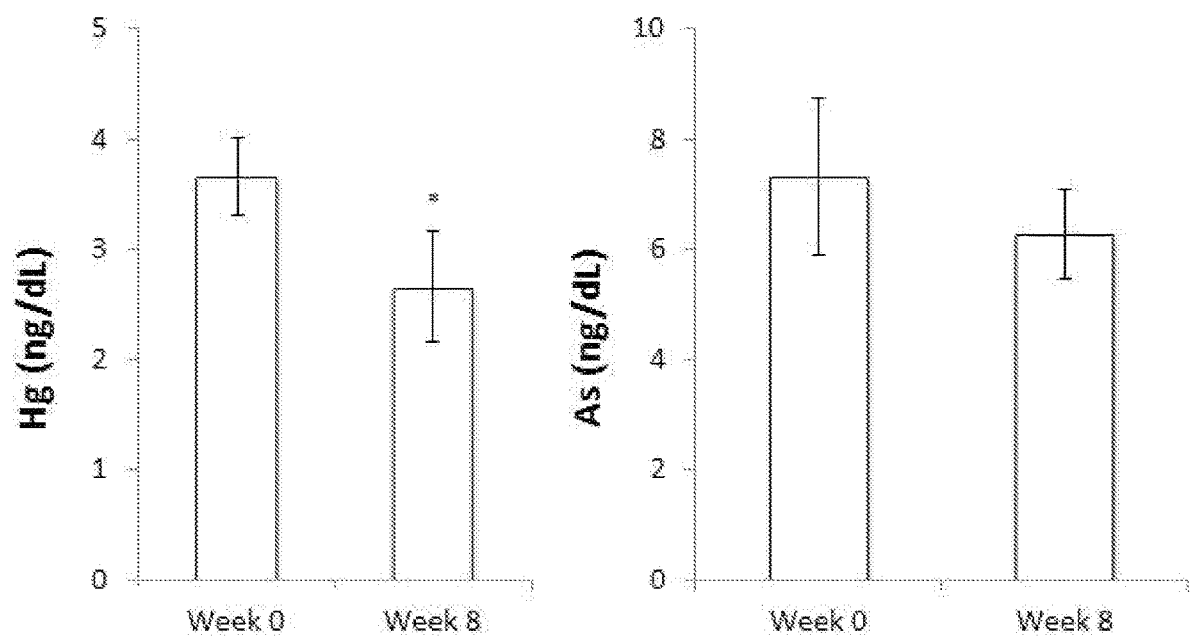
FIG. 1 shows the ability to reduce the content of hydrargyrum and arsenic in the blood of the green pear fruitlet extract in accordance with one embodiment of the present invention.

The data provided in the present invention represent approximated, experimental values that may vary within a range of ±20%, preferably ±10%, and most preferably ±5%.

Statistical analysis is performed using Excel software. Data are expressed as mean±standard deviation (SD), and the differences between these are analyzed by Student's t-test.

According to the present invention, the green pear variety is, but not limited to, *P. nivalis, P. bretschneideri, P. lindleyi* Rehder, or *P. pyrifolia* Nakai; preferably *P. nivalis, P. bretschneideri*, and *P. lindleyi* Rehder.

As used herein, the term "green pear fruitlet" means green pear fruit which is formed within 90 days after flowering of *P. nivalis, P. bretschneideri, P. lindleyi* Rehder, or *P. pyrifolia* Nakai, preferably is within 30-90 days.

The present invention provides a green pear fruitlet extract for preparing a composition for reducing the content of heavy metals in the blood and improving the pulmonary function. The green pear fruitlet extract is prepared by extracting a green pear fruitlet using water, alcohol, or a mixture of water and alcohol as a solvent. The green pear fruitlet extract can be used to reduce the content of heavy metals in human bodies, reduce the respiratory resistance, and increase the expiratory flow of human bodies.

Meanwhile, the composition comprising an effective amount of the green pear fruitlet extract and a pharmaceutical carrier of the present invention is for reducing the content of heavy metals in the blood and improving the pulmonary function and it is further. The composition is in a form selected from the group consisting of powder, granules, liquid, colloid, and cream, and can be made into, but is not limited to, a food, a drink, a drug, a reagent or a nutritional supplement.

The detailed extraction method of the young pear extract of the present invention, the test for reducing the content of heavy metals in the blood, the test for improving the forced vital capacity and the peak expiratory flow of humans are described in detail below to confirm the effect of the green pear fruitlet extract on reducing the content of heavy metals in the blood and improving the pulmonary function.

Example 1

Preparation of the Green Pear Fruitlet Extract

Pear is a generic term for the plants of *Pyrus*, which is usually a deciduous tree or a shrub. Only few species of pears are evergreen which belong to Maleae. The leaves of pears are mostly in shape of oval and vary in size depending on the species. The flower of them is white, or slightly yellowish and pink, with five petals. The shape of the fruit is round or with a thicker base than and a thin tail, which is commonly known as the "pear shape". The color of the fruit peel is different in varieties, and includes yellow, green, yellow with green, green with yellow, yellow brown, green brown, reddish brown, brown, and individual varieties could be purple red. Wild pears have smaller fruit diameters, which is between 1-4 cm, while artificially cultivated varieties can reach 8 cm in diameter and up to 18 cm in length.

The fruit of pear is usually for eating. It is not only delicious, but also sweet and nutritious. It contains a variety of vitamins and cellulose. The taste and texture of different variety of pears are completely different. Pears can be eaten raw or cooked. In terms of medical efficacy, pears can be used for constipation, digestive digestion, and cardiovascular benefits. The heated pear juice contains a large amount of anti-cancer polyphenols. In addition to being eaten as a fruit, pears can also be used as an ornamental fruit.

In one embodiment of the present invention, the green pear fruitlet is washed and coarsely ground using a homogenizer. Then, the green pear fruitlet is extracted using water, alcohol, or a mixture of water and alcohol as a solvent, preferably water. The weight ratio of the solvent to the green pear fruitlet at a ratio of 1:10-1:5. The extraction temperature is at 70-95° C. for 0.5-3 hours to obtain the crude extract of the green pear fruitlet. After the extraction, the crude extraction is cooled to room temperature. The crude extraction may be filtered through a 400 mesh filter to remove residual solids. Finally, the filtered green pear fruitlet may further be concentrated under reduced pressure (less than 1 atm) at 45-70° C. to obtain a concentrated product.

Example 2

Reduction the Content of the Heavy Metal in the Blood by Treatment of Green Pear Fruitlet Extract In order to investigate the effect of green pear fruitlet extract on the reduction the content of a heavy metal in the blood, 6 subjects were recruited to take 5-10 g of the green pear fruitlet extract of the present invention per day for 8 weeks. Next the blood of each subject was collected before and after taking the green pear fruitlet extract separately to take the detection of the content of the heavy metals in the blood, wherein the content of heavy metals in the blood of each subject is performed by the inspection unit.

The result of reducing the content of the heavy metal in the blood of subjects is shown in FIG. 1. Many studies show that excessive toxic elements of hydrargyrum in the body would cause irritability, insomnia, fatigue, memory loss, limb tremors, stomatitis, gastrointestinal and renal dysfunction, and reduction of immunity, etc. Other studies show that long-term exposure to toxic elements of arsenic could lead to peripheral blood vessels hardening (black foot disease), peripheral neuropathy, diarrhea, proteinuria, hyperkeratosis, pigmentation, bad breath, and stomatitis, etc. As showing in FIG. 1, after taking the green pear fruitlet extract of the present invention, the content of hydrargyrum in the blood is significantly reduced by 27.4% compared with that before taking the green pear fruitlet extract; besides, the content of arsenic in the blood is decreased by 14.3%. The results indicate that the green pear fruitlet extract of the present invention can effectively reduce the content of the heavy metal, hydrargyrum and arsenic, in human blood, and has the effect of reducing heavy metal toxin in human blood.

Example 3

Improvement of the Forced Vital Capacity (FVC) and the Peak Expiratory Flow (PEF) by Treatment of Green Pear Fruitlet Extract In order to investigate the effect of green pear fruitlet extract on the improvement of the forced vital capacity (FVC) and the peak expiratory flow (PEF), 6 subjects were recruited to take 5-10 g of the green pear fruitlet extract of the present invention per day for 8 weeks. Next the FVC and PEF of each subject was detected before and after taking the green pear fruitlet extract separately by the Mir Spirobank (Pinyork, Taiwan), wherein the FVC is an important index for measuring the resistance of the airway and the FVC is the maximum capacity of the subject to exhale and try to finish as much as possible after maximizing inspiration; and PEF is the maximum flow rate generated during exhalation. The lower respiratory resistance result in a greater FVC and a higher PEF.

Figure 2:
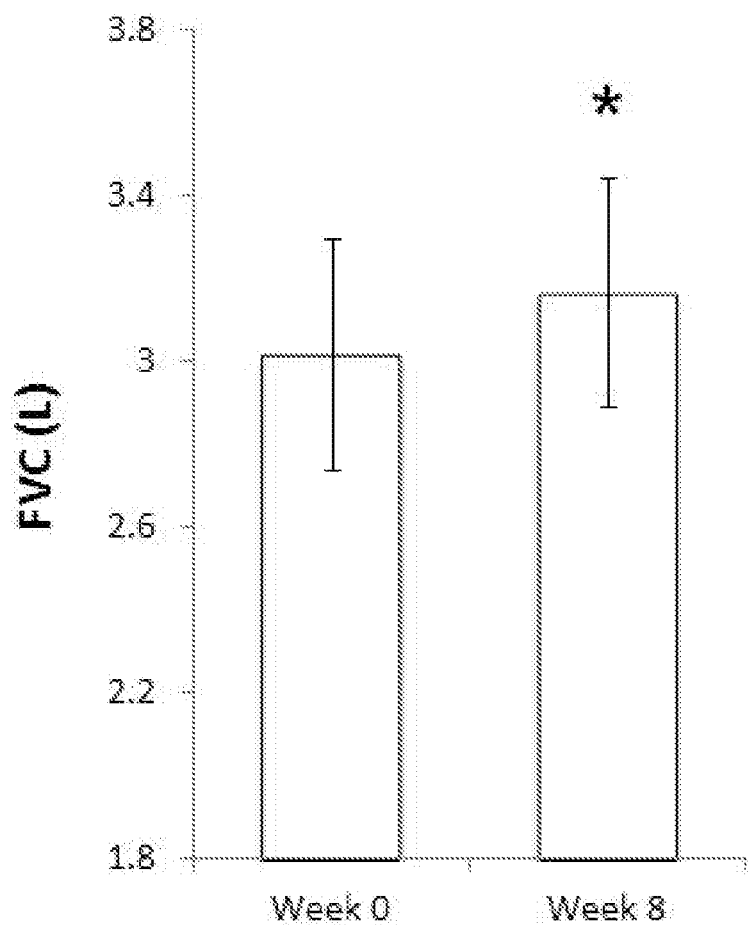
FIG. 2 shows the ability to improve the amount of the forced vital capacity (FVC) of the green pear fruitlet extract in accordance with one embodiment of the present invention.
Figure 3:
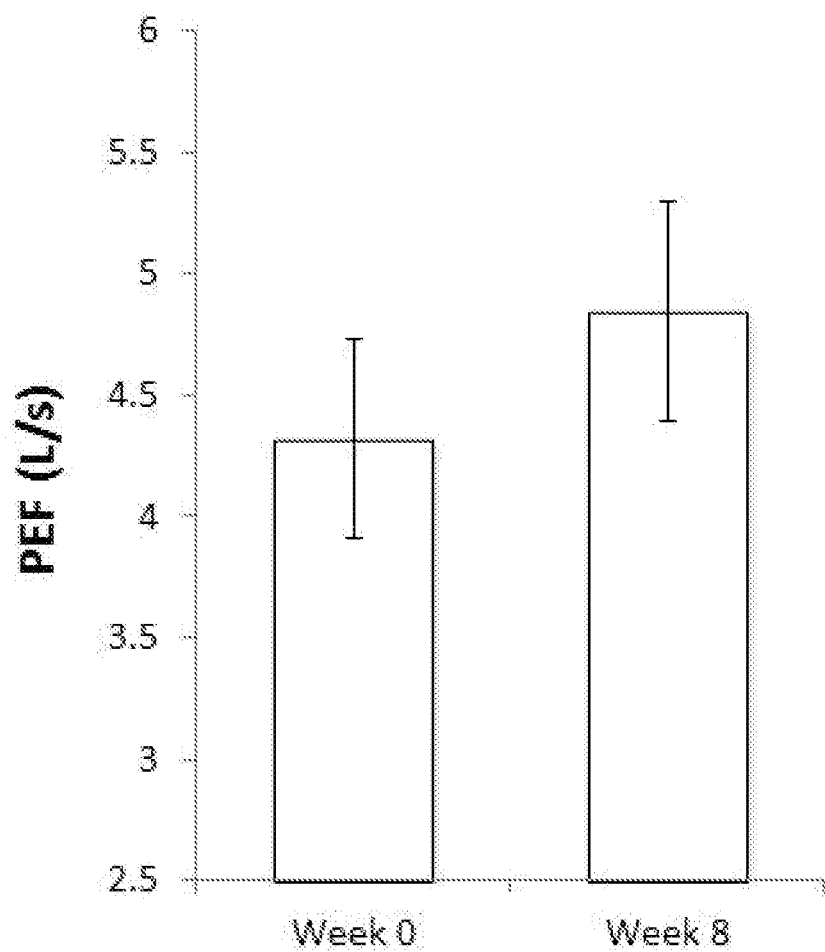
FIG. 3 shows the ability to improve the amount of the peak expiratory flow (PEF) of the green pear fruitlet extract in accordance with one embodiment of the present invention.

The result of increasing the FVC of the subjects is shown in FIG. 2; and the result of increasing the PEF is shown in FIG. 3. As showing the FIG. 2, after taking the green pear fruitlet extract of the present invention, FVC increases significantly by 5.0% (i.e. 0.15 L) compared with that before taking the green pear fruitlet extract. As showing in FIG. 3, PEF increases by 12.2% compared with that before taking the green pear fruitlet extract. The results indicate that the green pear fruitlet extract of the present invention can effectively enhance forced vital capacity and the peak expiratory flow of humans, and has the effects of reducing the respiratory resistance and increasing the expiratory flow of human bodies.

In summary, the green pear fruitlet extract of the present invention not only can effectively reduce the content of harmful heavy metals in human body such as hydrargyrum and arsenic, which are common in air pollution, but also can effectively improve forced vital capacity and the peak expiratory flow of humans to reduce the respiratory resistance and increase the expiratory flow. The green pear fruitlet extract of the present invention has the effects of preventing the harmful effects of heavy metals, smoothing the breathing and improving the pulmonary function. Therefore, the green pear fruitlet extract of the present invention can be used for preparing a composition for reducing the content of heavy metals in the blood and for improving the pulmonary function. When the green pear fruitlet extract of the present invention is prepared as a composition, the composition is in a form selected from the group consisting of powder, granules, liquid, colloid, and cream. The composition can be made into, but is not limited to, a food, a drink, a drug, a reagent or a nutritional supplement, which is administered to the body by oral administration, skin application, etc.

What is claimed is:

1. A method for reducing the content of heavy metal in the blood, comprising administering to a subject in need thereof a composition comprising a green pear fruitlet extract, wherein the green pear fruitlet extract is prepared by extracting a green pear fruitlet using water, alcohol, or a mixture of water and alcohol as a solvent.

2. The method according to claim 1, wherein the heavy metal is hydrargyrum or arsenic.

3. The method according to claim 1, wherein a liquid-to-solid ratio of the solvent to the green pear fruitlet is from 10:1 to 1:1.

4. The method according to claim 1, wherein the green pear fruitlet is extracted at a temperature from 70-95° C.

5. The method according to claim 1, wherein the green pear fruitlet extract is administered at a daily dosage of at least 5-10 g.

6. The method according to claim 1, wherein the composition is further added to a pharmaceutical carrier.

7. The method according to claim 1, wherein the composition is in a form selected from the group consisting of powder, granules, liquid, colloid, and cream.

8. A method for improving the pulmonary function, comprising administering to a subject in need thereof a composition comprising a green pear fruitlet extract, wherein the green pear fruitlet extract is prepared by extracting green pear fruitlet using water, alcohol, or a mixture of water and alcohol as a solvent.

9. The method according to claim 8, wherein the green pear fruitlet extract reduces the respiratory resistance and/or increases the expiratory flow of the subject in need thereof.

10. The method according to claim 8, wherein the green pear fruitlet extract increases the forced vital capacity (FVC) and the peak expiratory flow (PEF) of the subject in need thereof.

11. The method according to claim 8, wherein a liquid-to-solid ratio of the solvent to the green pear fruitlet is from 10:1 to 1:1.

12. The method according to claim 8, wherein the green pear fruitlet is extracted at a temperature from 70-95° C.

13. The method according to claim 8, wherein the green pear fruitlet extract is administered at a daily dosage of at least 5-10 g.

14. The method according to claim 8, wherein the composition is further added to a pharmaceutical carrier.

15. The method according to claim 8, wherein the composition is in a form selected from the group consisting of powder, granules, liquid, colloid, and cream.

* * * * *